United States Patent [19]

Vilasi

[11] Patent Number: 4,827,925

[45] Date of Patent: May 9, 1989

[54] CUFFLESS ADJUSTABLE ENDOTRACHEAL TUBE

[76] Inventor: Joseph A. Vilasi, 37 Wagon Wheel La., Dix Hills, N.Y. 11749

[21] Appl. No.: 149,786

[22] Filed: Jan. 29, 1988

Related U.S. Application Data

[63] Continuation-in-part of Ser. No. 920,752, Oct. 20, 1986, Pat. No. 4,722,335.

[51] Int. Cl.$^4$ .............................................. A61M 16/00

[52] U.S. Cl. ................................ 128/207.14; 128/343; 604/104

[58] Field of Search ...................... 128/200.26, 207.14, 128/207.15, 343; 604/104

[56] References Cited

U.S. PATENT DOCUMENTS 3,789,852 2/1974 Kim et al. ............................ 128/343

4,607,626 8/1986 Borodulin et al. .................. 128/343

FOREIGN PATENT DOCUMENTS 0240945 4/1969 U.S.S.R. ............................... 604/104

*Primary Examiner*—Paul T. Sewell

*Assistant Examiner*—Aaron J. Lewis

*Attorney, Agent, or Firm*—Leonard Belkin

[57] ABSTRACT

An expandable endotracheal tube and the like comprising extended, spaced segments. Actuating members fill the spaces between adjacent segments. The actuating members and the segments have curved edges so that sliding movement of the actuating members will cause the circumference of the tube to expand. A syringe type of device at the proximal end of the tube causes the actuating members to slide and effect the expansion of the segments.

21 Claims, 2 Drawing Sheets

CUFFLESS ADJUSTABLE ENDOTRACHEAL TUBE

This application is a continuation-in-part of my application Ser. No. 920,752 filed on Oct. 20, 1986, now U.S. Pat. No. 4,722,335.

BACKGROUND OF THE INVENTION

This invention relates to expandable endotracheal tubes and more generally to devices adapted to be inserted into a body opening for carrying out therapeutic and other medical procedures.

An endotracheal tube typically is employed for insertion in a patient through his mouth for the purpose of ventilating his lungs. The tube passes through the normally restricted glottis or passageway between the vocal chords and may terminate adjacent the entrance to the bronchial tubes. To insure proper delivery to the lungs of the gases employed in the ventilation procedure, a cuff mounted on the far or distal end of the tube is inflated in situ to prevent back flow around the tube.

To accommodate patients having differently sized trachea, there is generally available to the medical practitioner a variety of endotracheal tubes of different diameters to permit selection of the proper size tube for the patient. In order to provide the most unobstructed passageway to the lungs it is desirable to insert the largest possible diameter tracheal tube acceptable to the patient.

Factors which limit the size of tube which can be utilized for a particular patient include the glottic passageway and the presence of the cuff on the outside of the distal end of the tube. Another factor is that the endotracheal tubes come in discrete sizes. To avoid possible damage to the vocal chords, it is quite often in the interest of the safety of the patient necessary to insert a smaller sized tube than the patient could safely tolerate because the next larger size is unacceptable.

In the case of children the vocal chord openings are narrower than in adults so that there is a further restriction on the size of the diameter which can be employed, and in some children it is not possible or feasible to employ the cuff to prevent the backflow.

In addition, in some situation, the endotracheal tube must be inserted through the nose which limits further the diameter which can be tolerated.

In my U.S. Pat. No. 3,968,800 there is disclosed an adjustable endotracheal tube which was designed to overcome the problems and drawbacks associated with existing endotracheal tubes. The patented arrangement is complex and lacks the flexibility necessary to accommodate sufficiently well the varying shapes or trachea found in different patients.

In my U.S. application Ser. No. 920,752 there is shown an expandable endotracheal tube split into logitudinal, overlapping sections and provision for a gas under pressure to be applied to slide the overlapping sections with respect to each other to enlarge the diameter of the tube to fill the body opening, thereby avoiding the need for a cuff. At the present state of technology it has been found that the physical requirements of the embodiments shown in my earlier application are such that the cost of making such expandable tubes are prohibitive based upon the present state of the art.

SUMMARY OF THE INVENTION

This invention overcomes or reduces many of the problems associated with endotracheal tubes and the like now in use and expandable tubes which have been proposed for use.

In the present invention it is possible to insert the endotracheal tube and then to expand it to exactly the glottic size of the patient until all back flow ceases. In addition, an important feature of this invention is the more simple and economic construction as compared to previous such devices combined with a higher degree of reliability due to the all mechanical configuration. With this arrangement, blackflow is completely eliminated without the need for the use of an inflatable cuff.

One preferred embodiment of this invention is a device for insertion into a body opening comprising an extended tube-like member made up of longitudinal segments separated by rigid actuating members which increase the separation of the segments to enlarge the diameter of the tube when moved along the longitudinal axis of the tube. Adjacent the proximal end of the device is located actuator means similar in configuration to a syringe to cause the movement of the actuating members. In this arrangement expansion of the circumference is limited only by the space within the patient. Provision is included to lock the tube in its expanded state. Removal of the device is facilitated by unlocking the tube which permits its relaxation to facilitate withdrawal of the tube-like member from the body opening.

Other embodiments of this invention involve other configurations in which the same principles are incorporated.

It is thus a principal object of this invention to provide an endotracheal tube and the like of simple and reliable construction which can be expanded in situ.

Other objects and advantages of this invention will hereinafter become obvious from the following description of preferred embodiments of this invention.

DETAILED DESCRIPTION OF THE PREFERRED EMBODIMENTS

In the following description of the preferred embodiments, it is understood that while the devices described are endotracheal tubes the invention is equally applicable to other devices for insertion into body openings such as bronchoscopes, vascular and cervical dilators, and the like. In addition, while reference is made to tubes or tube-like members, it is understood that the cross section may be circular, oval, or any other configuration suitable for the particular application to which the principles of this invention are applicable.

Figure 1:
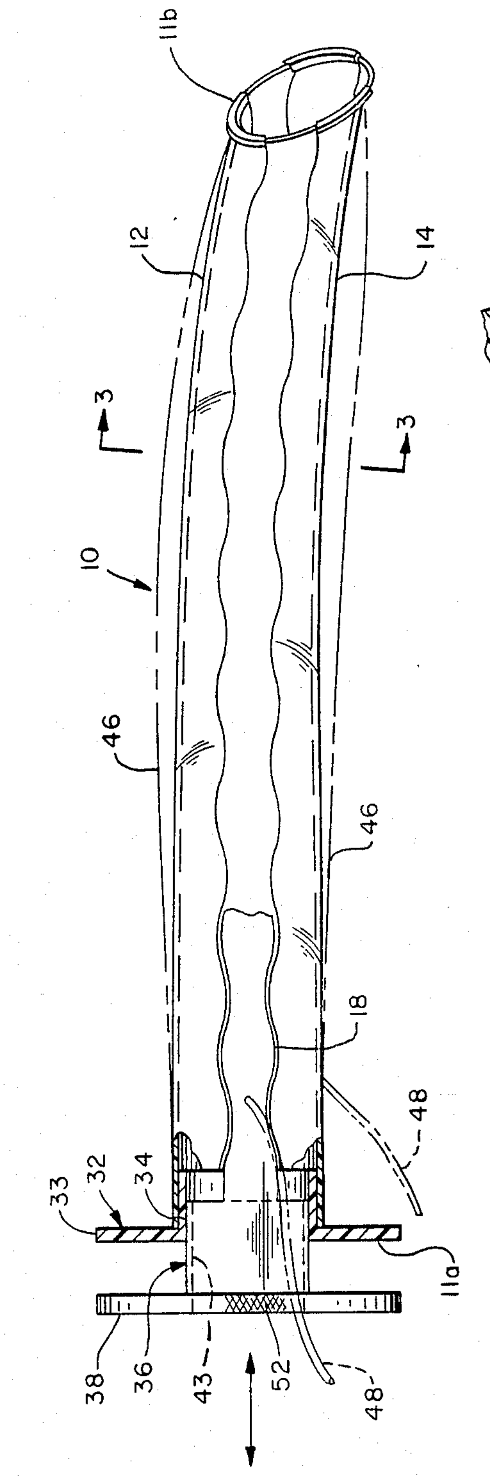
FIG. 1 is an isometric view partially cut away of an endotracheal tube embodying the principles of this invention.
Figure 3:
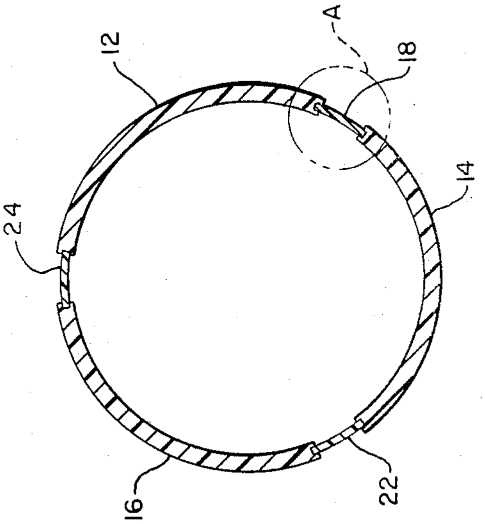
FIG. 3 is a view along 3—3 of FIG. 1.

Referring to FIGS. 1 and 3 there is shown an endotracheal tube 10 which embodies the principles of this invention. Tube 10 has an overall configuration similar to that of the conventional endotracheal tube having a generally arced shape with a proximal end 11*a* and a distal end 11*b*, the latter cut at a bias for facilitating the discharge of the gas being employed for ventilating the lungs of the patient. When tube 10 is inserted into the patient through the oral or nasal cavity, distal end 11*b* would terminate in the trachea adjacent the entrance to the bronchial tubes, while the proximal end 11*a* would extend out from the mouth or nose of the patient. Not shown are the conventional adaptors which would plug in or otherwise be attached to proximal end 11*a* for supplying the ventilating gas.

In this embodiment, tube 10 consists of three elongated segments 12, 14, and 16 separated by extended actuators 18, 22, and 24. Segments 12, 14 and 16 are preferably made from an elastomeric material such as rubber, soft linear thermo plastic such as polyethylene or polypropelene and the like enabling it to be inserted and conform to the shape of the body opening into which tube 10 is being inserted. Depending on the thickness of the walls making up tube 10, the degree of flexibility of the device can be selected for purposes to be described below. Extended actuators 18, 22 and 24 are made from somewhat more rigid material as will be more particularly described below.

Segments 12, 14 and 16 are shaped along their oppositely facing, mirror-imaged edges as a sine wave forming camming surfaces. Actuators 18, 22, and 24 fill the spaces between segments 12 and 14, 14 and 16, and 16 and 12, respectively, as seen in FIG. 1. Actuators 18, 22 and 24 fill the spaces exactly and act like cams when actuated in the manner described below. The spaces between the actuators and the segments shown in FIG. 1 and FIG. 3 are only to clarify the details of construction. Actually the parts fit together exactly in a manner to be described below.

Figure 4A:
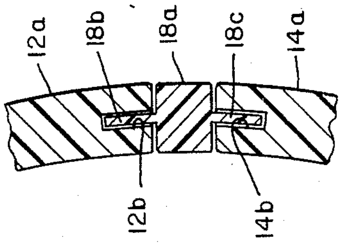
FIG. 4*a* is a view similar to FIG. 4 showing an alternative actuator design.
Figure 4:
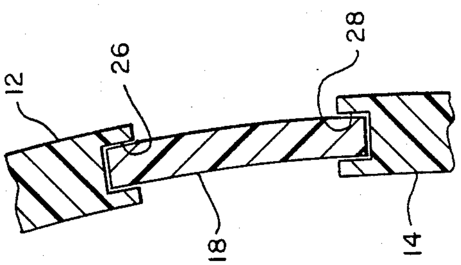
FIG. 4 is an enlarged view of the area designated A in FIG. 3.

To insure that actuators 18, 22 and 24 remain engaged with segments 12, 14 and 16, the latter are provided with channels to accomodate the actuators as illustrated in FIG. 4 for actuator 18. It will be noted that segments 12 and 14 are provided with channels 26 and 28, respectively, to accomodate actuator 18 which is therefore thinner than the thickness of segments 12 and 14. The remaining actuators are similarly mounted.

Figure 2A:
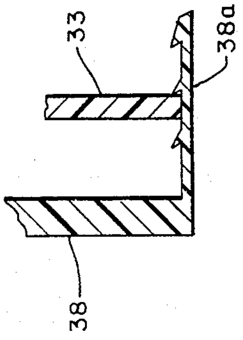
FIG. 2*a* is a detail of FIG. 2 showing an alternative locking design.
Figure 2:
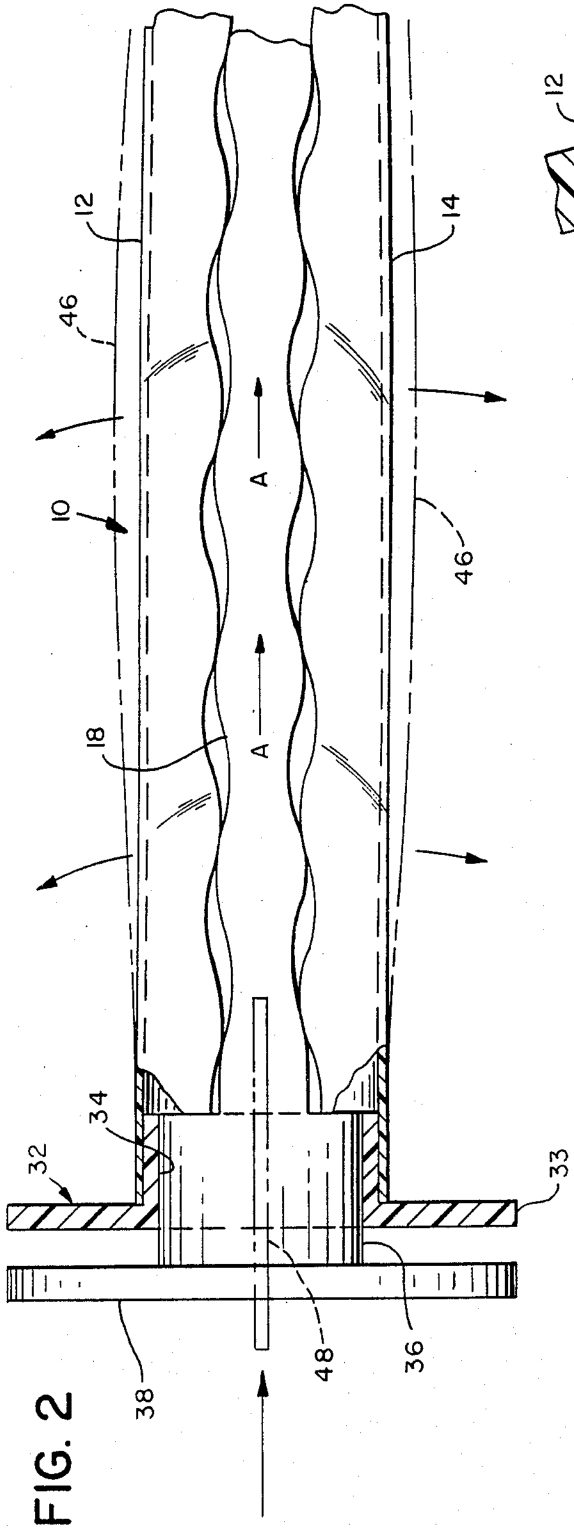
FIG. 2 is a partial view similar to that of FIG. 1 with the tube fully expanded.

It should be noted at this point that when actuator 18 is urged to the right as seen by arrows A in FIG. 2, a camming action will occur which will cause the space between segments 12 and 14 to widen. When all three actuators 18, 22 and 24 are simultaneously moved in the same direction this will effectively increase the overall diameter of endotracheal tube 10 along its whole length.

To effect this change in diameter in situ, reference is made to FIGS. 1 and 2 where is shown that at the proximal end 11*a* tube 10 terminates in an endpiece 32 having a flange 33 and having an opening 34 giving access to the interior of tube 10.

Inserted into opening 34 is a cylindrical member 36 with a flange 38 with the former extending into opening 34 of endpiece 32. Attached to and extending from member 36 are actuators 18, 22, and 24. It should be noted that actuators 18, 22 and 24 are sufficiently flexible so that they are expanded slightly from their attachment to cylindrical member in order to enter the grooves in segments 12, 14, and 16 as seen in FIG. 4.

Cylindrical member 36 and endpiece 32 function together in a manner similar to a syringe. That is, as seen in FIG. 1, when flange 33 is straddled by two fingers and a thumb is placed on flange 38 in the manner of a syringe and squeezed, then as seen in FIG. 2, actuators 18, 22 and 24 are urged toward the right as shown by arrows A to cause the diameter of tube 10 to enlarge.

The circular opening 43 within hollow cylindrical body 36 would be a standard size to receive an adaptor (not shown) for the supply of ventilating gas.

In FIG. 1 it will be seen that the proximal ends of segments 12, 14 and 16 flare out to enclose the cylindrical portion of endpiece 32. When tube 10 is fully expanded as seen in FIG. 2, tube 10 is approximately the diameter of the cylindrical portion of endpiece 32.

In order to prevent leakage of ventilating gas out the sides of tube 10 and also to hold the distal ends of segments 12, 14 and 16 from coming apart, a thin envelope or membrane 46 of impermeable latex material would be employed. Envelope 46 would be cylindrical and sealed at the proximal end of tube 10 to endpiece 32 and at the distal end to the edges of segments 12, 14 and 16 and stretched across the spaces between the segments. At distal end 11*b*, as noted, membrane 46 would also serve the purpose of keeping that end of tube 10 from coming apart.

In the construction of tube 10, the internal diameter typically would start out about 7 mm. and expand to a maximum of about 10.5 mm.

In order to insure that tube 10 remains in the expanded state during the ventilation procedure, latex envelope 46 may be provided with one or more flexible tabs 48 attached to envelope 46 at one end and having a Velcro surface. A matching Velcro surface 52 would be on the outside of flange 38 so that tab 48 could be stretched to make the engagement and thereby to lock the actuators in place, as seen in FIG. 2.

In the operation of the apparatus just described, in the initial state of endotracheal tube 10 as seen in FIG. 1, the latter is inserted into the trachea of the patient in usual fashion, as previously described. After tube 10 is properly positioned, flanges 33 and 38 are squeezed to enlarge the diameter of tube 10 as far as it will go within the trachea. Tabs 48 are connected to flange 38 using the Velcro to hold the actuators in place. Then the ventilating adaptor (not shown) is plugged into cylindrical opening 43 and the ventilation procedure can be initiated.

Instead of utilizing tabs 48 to secure the locking of actuators 18, 22, and 24 an alternative arrangement such as that shown in FIG. 2*a* may be utilized. In this arrangement, flange 38 may be provided with one or more toothed extensions 38*a* located around its periphery to engage flange 33. When flanges 33 and 38 are squeezed together to enlarge tube 10, clicks will be felt as the outer edge of rim 33 passes over the teeth on each extension 38*a*. To release tube 10, the technician would merely pull extensions 38*a* outwardly.

It will be noted from FIG. 4 that actuators 18, 22 and 24 are not as thick as segments 12, 14 and 16 in order to ride in the slots provided.

Under certain circumstances it may be desirable to have the actuators at the same thickness as the segments in order to provide a smoother outer surface. Such a configuration is shown in FIG. 4*a* wherein actuator 18*a* is shown at such a thickness with a pair of thin, blade like extensions 18*b* and 18*c* riding in slots 12*b* and 14*b*, respectively, of segments 12*a* and 14*a* which are otherwise identical to segments 12 and 14 of FIGS. 1 and 2. Extensions 18*b* and 18*c* are integral with actuator 18*a* but are sufficiently hard or rigid to carry out the function described for them. The remaining structure is identical to that of FIGS. 1–4, that is, there would be an additional segment and actuators identical to that iof *12a*, *14a*, and *18a*.

The arrangements shown in the figures for moving actuators 18, 22, and 24 utilize a syringe type device. If desired alternative means can be provided for this purpose, for example, the use of a screw type device threadably engaged with the actuators. In this case, the technicians or physician would rotate a portion of the device to expand tube 10. In addition it may be desirable in some circumstances to pull the actuators (that is, opposite to the direction shown by arrows A in FIG. 1) instead of pushing them as is illustrated and has been described. In such an arrangement, tabs 48 shown in FIGS. 1 and 2 would be of rigid material to maintain the expansion until it is time to withdraw tube 10, and in FIG. 3, the teeth would be directed in the opposite direction that that shown.

The embodiments described are made up of three segments. If desired, four or more segments could be employed which would render the device more circular in cross section. The more segments which are employed the smoother or more continuous outer surface can be obtained.

While only preferred embodiments of this invention has been described it is understood that many variation of the invention are possible without departing from the principles of this invention, as defined in the claims which follow.

What is claimed is:

1. An endotracheal tube comprising:

a. an extended hollow tube being segmented along its length comprising elongated segments forming the wall of said hollow tube with spaces between adjacent segments;

b. actuator means extending substantially the full length of said hollow tube between adjacent segments occupying said spaces in the wall of said hollow tube;

c. means in response to axial movement of said actuator means for effecting the expansion of said endotracheal tube simultaneously and substantially equally over the whole length of said hollow tube; and d. drive means adjacent the proximal end of said hollow tube for effecting the axial movement of said actuator means relative to said segments.

2. The endotracheal tube of claim 1 wherein said segments include camming surfaces along their lengths facing the camming surfaces of adjacent segments.

3. The endotracheal tube of claim 2 wherein said actuator means include surfaces along the lengths thereof to engage said camming surfaces whereby said expansion is caused by camming action.

4. The endotracheal tube of claim 3 having means to enclose said hollow tube to seal said hollow tube against leakage.

5. The endotracheal tube of claim 4 including lock means to prevent collapse of said tube after expansion is complete.

6. The endotracheal tube of claim 3 in which said drive means includes a first cylindrical member connected to said segments and a second cylindrical member sliding within said first cylindrical member connected to said actuator means, and rim means connected to each of said cylindrical members to permit said second cylindrical member to be moved within said first cylindrical member to enlarge said endotracheal tube.

7. The endotracheal tube of claim 6 having envelope means to enclose said hollow tube to seal said hollow tube against leakage.

8. The endotracheal tube of claim 7 having means to lock said hollow tube in its expanded state.

9. The endotracheal tube of claim 8 in which said lock means includes means extending from said envelope means to engage said rim means on said second cylindrical member.

10. The endotracheal tube of claim 8 in which said lock means includes means extending from the rim means of said second cylindrical member to engage the rim means on said first cylindrical member.

11. The endotracheal tube of claim 7 in which said envelope means joins the proximal end of said hollow tube to the distal end off said hollow tube and prevents separation of said segments at said distal end.

12. The endotracheal tube of claim 11 in which said camming surfaces of said segments are provided with slots, said actuator means including means riding in said slots.

13. The endotracheal tube of claim 12 in which surfaces are sine wave in shape along the lengths of said segments and actuator means whereby movements of said actuator means causes said camming action.

14. A device for insertion into a body opening comprising:

a. an extended hollow tube comprising a plurality of extended, transversely curved and spaced segment means forming the wall of said hollow tube with the spaces between adjacent segment means extending the length of said hollow tube;

b. actuator means occupying the spaces in the wall of said hollow tube between adjacent segment means and extending substantially the full length of said hollow tube;

c. means mounted in the proximal end of said hollow tube for effecting the sliding movement of said extended actuator means; and d. means responsive to each movement of said extended actuator means for increasing the separation of said segment means thereby expanding the circumference of said hollow tube substantially equally and simultaneously over the whole length of said hollow tube.

15. The device of claim 14 in which each said segment means includes camming surfaces facing adjacent, spaced segment means.

16. The device of claim 15 in which said means for increasing said separation comprises cam members engaged with said camming surfaces.

17. The device of claim 16 in which said camming surfaces have a sine wave configuration.

18. The device of claim 17 in which said cam members have sine wave configurations on each side to engage adjacent segment means.

19. The device of claim 14 in which said means mounted on said proximal end comprises stationary means connected to said segment means.

20. The device of claim 19 in which said means mounted on said proximal end also comprises slidable means mounted in said stationary means connected to said actuator means.

21. The device of claim 20 having means to permit movement of said slidable means with respect to said stationary means to effect expansion of said tube-like means.

* * * * *